United States Patent [19]

Dosmann et al.

[11] Patent Number: 4,890,926
[45] Date of Patent: Jan. 2, 1990

[54] REFLECTANCE PHOTOMETER

[75] Inventors: Andrew Dosmann, Mishawaka; Willis Howard, Osceola, both of Ind.; Alfred Zembrod, Gladbach, Fed. Rep. of Germany

[73] Assignee: Miles Inc., Elkhart, Ind.

[21] Appl. No.: 135,252

[22] Filed: Dec. 21, 1987

[51] Int. Cl.⁴ ............................................. G01N 21/47
[52] U.S. Cl. ...................................... 356/369; 356/446
[58] Field of Search ............... 356/364, 369, 445, 446, 356/448, 370, 402, 416

[56] References Cited

U.S. PATENT DOCUMENTS

| 2,947,212 | 8/1960 | Woods | 356/369 |
| 3,565,568 | 2/1971 | Hock | 356/369 |
| 3,790,286 | 2/1974 | Kraus | 356/369 |
| 3,807,868 | 4/1974 | Simila | 356/369 |
| 4,482,250 | 11/1984 | Hirvonen et al. | 356/369 |
| 4,632,559 | 12/1986 | Brunsting | 356/446 |
| 4,676,653 | 6/1987 | Strohmeier et al. | 356/446 |
| 4,701,052 | 10/1987 | Schoen | 356/369 |

FOREIGN PATENT DOCUMENTS 231402 12/1984 Japan ................................. 356/369

OTHER PUBLICATIONS

Mardix, S., "Polarized Reflected Light for Contrast Enhancement in Underexposed Radiographs", *Journal of Applied Physics*, vol. 46, No. 2, (Feb. 1975) pp. 773-774.

Primary Examiner—Richard A. Rosenberger
Attorney, Agent, or Firm—Roger N. Coe

[57] ABSTRACT

A reflectance photometer for quantitatively measuring diffuse light includes a light source located above a sample. The reflectance photometer also includes a first detector mounted at a preselected scattering angle relative to an axis extending perpendicularly from the sample through the light source. A first linear polarizer is mounted between the sample and the light source. The direction of polarization of the first linear polarizer is vertical to a scattering plane defined by the direction of incoming light from the light source and the direction of reflected light detected by the first detector. A second linear polarizer is mounted between the sample and the first detector. The direction of the second polarizer is parallel to the scattering plane. The reflectance photometer can include a second detector mounted at a second, scattering angle. A third linear polarizer is mounted between the sample and the second detector. The direction of polarization of the third linear polarizer can be perpendicular or parallel to the scattering plane. Generally, the three polarizers are close such that the contributors of scattered light as related to surface noise will be minimized for the first detector and maximized for the second detector, respectively. The optimum settings of the polarizer will depend on the settings of the polarizers, the scattering geometry, the sample orientation and the bulk and surface scattering properties of the sample material.

4 Claims, 2 Drawing Sheets

REFLECTANCE PHOTOMETER

BACKGROUND OF THE INVENTION

A. Field of the Invention

The present invention relates to reflectance photometers, and, more particularly, the present invention relates to reflectance photometers in which the light of absorption is modulated by linear polarizers.

B. Description of the Background Art

Reflectance photometers commonly are used for quantitative chemical analysis, such as analysis of body fluids. A known quantity of body fluid, such as a drop of blood, is placed on a reactive reagent strip impregnated with a chemical reactive with a quantitatively unknown body fluid component, e.g. blood glucose. The fluid is wiped off the strip and the reagent strip is placed within or in contact with a readhead of a reflectance photometer where the strip is illuminated with a controlled, diffuse light and the light reflected from the strip is measured. The reaction product formed on the reagent strip will reflect a known amount of light for each different amount (concentration) of each body fluid component analyzed. The light reflected is sensed by a detector in the readhead. Thus, for each different reflection measured from the reagent strip, the quantity of the particular body fluid component in the sample analyzed is known.

Even though present generation reagent strips have reached a high degree of perfection, they still show a number of intrinsic drawbacks. For example, there is reduced resolution at higher glucose levels, and the light levels of scattered light become separated by lower and lower margins the higher the glucose level within the body fluid to be determined. This highly nonlinear response of reagent strips leads to an upper linear and of sensitivity of measurable glucose concentrations; for example, there are some reagent strips the sensitivity of which does not exhaust beyond 400 mg/dL. It is possible to modify the reagent pads chemically to overcome these drawbacks but chemical modification is difficult and expensive. It is desireable to overcome these drawbacks using an entirely new procedure not requiring chemical modification.

SUMMARY OF THE INVENTION

An object of the present invention is to provide a new and improved reflectance photometer.

Another object of the present invention is provide a new and improved method for improving the performance of reflectance photometers.

A further object of the present invention is to provide a new and improved reflectance photometer that has increased resolution at higher glucose levels.

Still another object of the present invention is to provide a new and improved reflectance photometer with a sensitivity range beyond 400 mg/dl.

Another objective of the present invention is to provide an improved reflectance photometer capable of recognizing surface imperfections of sample strips and for rejecting such samples as improper.

Another objective of the present invention is to provide an improved reflectance photometer capable of reducing surface related noise contributions to the level of scattered light to a minimum amount.

Another object of the present invention is to provide a new and improved reflectance photometer that can detect high and low concentrations without requiring reagent strips with two reagent pads.

A further object of the present invention is to provide a new and improved reflectance photometer including optical polarization.

Briefly, the present invention is directed to a new and improved reflectance photometer using optical polarization for increased sensitivity. The reflectance photometer includes the conventional components of known reflectance photometers such as a light source and a detector. Improved performance and sensitivity result in the present invention from the inclusion of a first linear polarizer mounted between the light source and a sample positioned in the reflectance photometer, and the inclusion of a second linear polarizer between the sample and the detector. In one embodiment of the present invention, the direction of polarization of the first linear polarizer is perpendicular to the direction of polarization of the second linear polarizer. Depending on the requirements for the reflectance photometer, however, the direction of polarization of the first linear polarizer can be parallel to the direction of polarization of the second linear polarizer.

In another embodiment of the present invention a second detector is included in the reflectance photometer. A third linear polarizer is mounted between the sample and the second detector. The direction of polarization of the third linear polarizer can be perpendicular or parallel to the direction of polarization of the first linear polarizer depending on the requirements of the reflectance photometer.

BRIEF DESCRIPTION OF THE DRAWINGS

Other and further objects, advantages and features of the present invention will be apparent to those skilled in the art from the following detailed description taken in conjunction with the accompanying drawings in which.

DESCRIPTION OF THE PREFERRED EMBODIMENTS

Reagent strips for measuring substrates such as glucose in body fluids, are well developed but use of these strips in current reflectance photometers have some drawbacks. For example, reduced resolution is experienced at higher glucose levels in the fluid being measured; the sensitivity range of many strips does not extend beyond 400 mg/dl; and two reagent pads each with a different chemistry are sometimes required to measure low and high substrate concentrations. In the past, performance of reflectance photometers readheads has been improved by modifying the chemistry of the reagent pads. One procedure has been to increase the number of light scatters in the reagent pads. To date, modifying the readhead of a reflectance photometer to improve the performance has not been considered.

Figure 1:
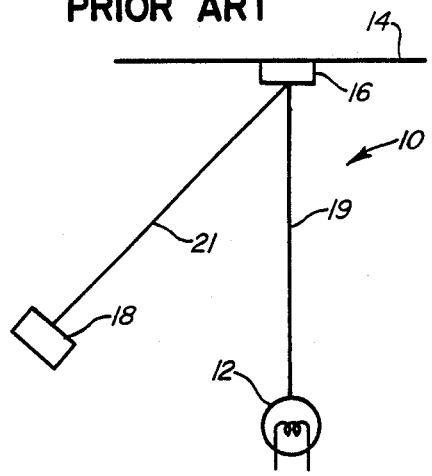
FIG. 1 is a schematic illustration of a prior art reflectance photometer readhead.

A typical prior art readhead is schematically illustrated in FIG. 1. The prior art readhead is generally designated by the reference numeral 10. The readhead 10 includes a thermal light source 12. Light from the light source 12 is directed onto a sample 14 that can be a reagent strip with a reagent pad 16. Light impinging on the reagent pad 16 is absorbed to varying degrees and reflected in a scattered pattern. Some of the reflected light is detected by a detector 18 which can be a photoelectric detector.

The present invention includes modifying a typical prior art readhead to improve performance. The modification, however, does not significantly change the structure of the typical readhead and does not significantly increase the cost of the readhead. The invention involves modulating the light of absorption through the use of linear polarizers. Beams of light have an electric vector that is transverse or perpendicular to the line of travel of the beam. In unpolarized light, the electric field of light is distributed in all directions. Linear polarizers filter light in a selected direction allowing passage of only that light having an electric vector in the selected direction. Light can be polarized vertically, or horizontally relative to a scattering plane or randomly.

Figure 6:
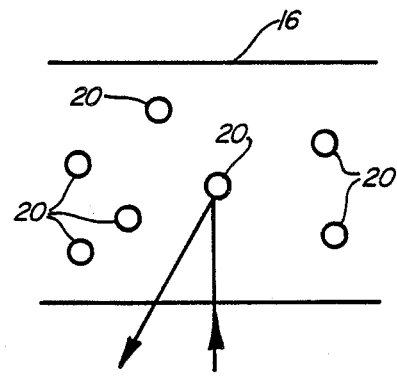
FIG. 6 is a schematic illustration of a single light scattering event in a film matrix including embedded light scattering particles.

To understand the effect of linear polarizers in a readhead it is helpful to understand what happens to light impinging on a reagent pad. The chemicals in reagent pads typically include titanium dioxide or barium sulfate particles. These particles scatter or reflect light that hits them. This scattered or reflected light is measured by the detector 18 and data corresponding to the intensity of the light is analyzed to determine the concentration of selected substrates such as glucose. As light from light source 12 travels in the reagent pad 16 (FIGS. 6 and 7), the light is scattered and some of the light is absorbed by dye molecules resulting in a reduction in the intensity of the reflected light detected by the detector 18. The scattering process results in changes in the polarization of the light.

Figure 7:
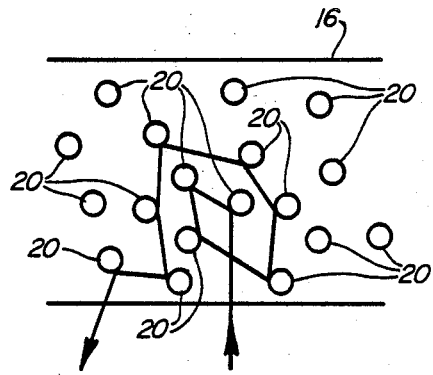
FIG. 7 is a schematic illustration similar to FIG. 6 illustrating a multiple light scattering event.

There are generally two types of scattering events or processes, single (FIG. 6) and multiple (FIG. 7). In the single light scattering event (FIG. 6), light strikes a single or only a few light reflecting particles 20 and is reflected out of the pad 16 toward detector 18. During this event, there is typically little change in the polarization of the light. In a multiple scattering event (FIG. 7), light strikes several light reflecting particles 20 before leaving the pad 16. The multiple light scattering event is more likely to result in a change in the polarization of the light. An additional result of a multiple light scattering event is there is greater absorption of the light due to the longer path length of the light through the pad 16.

Understanding that multiple light scattering events result in the change of polarization of the light, a modified readhead generally designated by the reference numeral 110 may be used to improve the performance of the readhead. The modified readhead 110 includes a thermal light souree 12 for producing light that impinges on a sample or reagent strip 14 which includes a reagent pad 16. The modified readhead 110 also includes a detector 18. The detector 18 is mounted in the modified readhead 110 at a scattering angle "x". It has been determined that the most efficient scattering angle is forty-five degrees as measured between the line 19 representing the direction of travel of the incoming light from the light source 12 to the sample 14 and the line 21 representing the direction of travel of the reflected light from the sample 14 to the detector 18. Other scattering angles can also be used.

Figure 2:
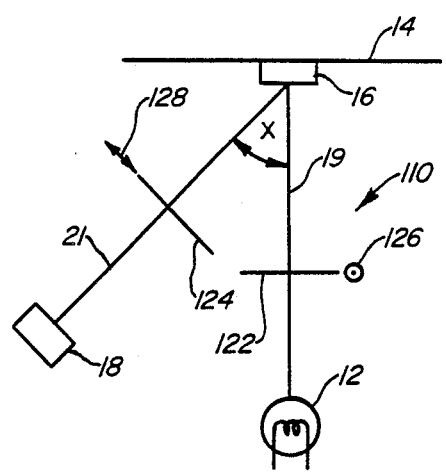
FIG. 2 is a schematic illustration of a first embodiment of a reflectance photometer readhead constructed in accordance with the principles of the present invention with first and second linear polarizers each having a direction of polarization parallel to and vertical to, respectively, a scattering plane defined by the direction of the incident light from a source of light toward a sample and the direction of light reflected from the sample toward a detector.

The readhead 110 differs from prior readheads 10 by the inclusion of a first linear polarizer 122 mounted in the readhead 110 between the pad 16 and the light source 12 and a second linear polarizer 124 mounted in the readead 110 between the pad 16 and the detector 18. The linear polarizers 122 and 124 can be Polaroid foil polarizers of the type used in cameras. In the embodiment of the modified readhead 110 illustrated in FIG. 2, the direction of polarization of the first linear polarizer 122 is vertical to a scattering plane defined by the direction of the incoming light (light from the light source 12 to the pad 16) and the direction of the outgoing or reflected light (light from the pad 16 and the detector 18). The vertical direction of polarization is indicated by the symbol designated by the reference numeral 126. The direction of polarization of the second linear polarizer 124 is parallel to the scattering plane. The parallel direction of polarization is perpendicular to the direction of polarization of the first linear polarizer 122. The parallel direction of polarization is indicated by the symbol designated by the reference numeral 128 in FIG. 2. This orientation of the polarizers 122 and 124 is termed v-p.

With the v-p orientation of the polarizers 122 and 124 the detector 18 will only detect reflected light whose polarization has changed by at least ninety degrees from the polarization of the incoming light 19. If the change in polarization has been less than ninety degrees, some of the light reflected from pad 16 will be filtered by the second linear polarizer 124. Since the multiple light scattering event (FIG. 7) changes the polarization of the light more so than single scattering events, light detected by detector 18 in the v-p orientation of the polarizers 122 and 124 will have had a longer path length in the pad 16 and there will have been greater absorption.

Figure 3:
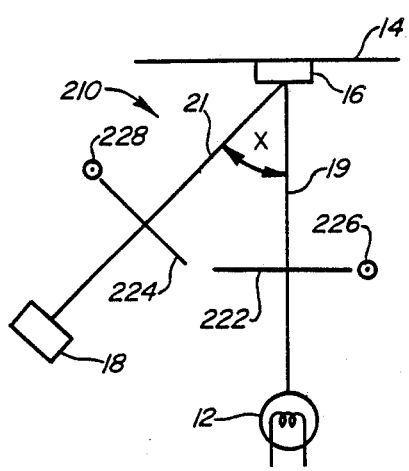
FIG. 3 is a schematic illustration similar to FIG. 2 with the direction of polarization of the first linear polarizer being vertical to the scattering plane and the direction of polarization of the second linear polarizer also being vertical to the scattering plane.

In an alternative embodiment (FIG. 3), a modified readhead 210 with a light source 12, a sample 14 with a reagent pad 16, and a detector 18 includes a first, linear polarizer 222. The first linear polarizer 222 is of a vertical orientation as indicated by the symbol 226. A second linear polarizer 224 is also provided. The second linear polarizer 224 is also of a vertical orientation as indicated by the symbol designated by the reference numeral 228. This arrangement of the first and second linear polarizers is termed the v-v orientation, and the directions of polarization of the linear polarizers 222 and 224 are parallel. The v-v orientation will predominately detect reflected light from single scattering events (FIG. 6) in which there has been little absorption of light and less than a ninety degree change in polarization.

The preferred orientation of linear polarizers is v-p. Using this orientation, several disadvantages experienced in prior art readheads 10 are eliminated. In prior art readheads 10 the dynamic range of reflectance values for higher glucose concentration levels is narrowly spaced. This makes accurate measurements by the reflectance photometer difficult. If the dynamic range could be widened, the accuracy of measurements could be increased. It has been determined that the v-p orientation (FIG. 2) significantly increases the sensitivity of reflectance photometers by widening the dynamic range of reflectance values resulting in more accurate readings by the instrument.

This increased sensitivity is due to the fact that reagent pads 16 have many small fibers extending randomly from the surface of the pad 16 or other surface irregularities. When measuring scattered light in the high concentration range, there is maximum absorption of the light in the pad 16 but there is also considerable light scattered off the fibers or other surface irregularities. Since the fibers or other surface irregularities do not carry significant amounts of color, the light scattered by the fibers is not related to the effect (absorption) sought to be measured by the instrument and is considered surface noise. If there is significant absorption in the pad, the signal sought to be measured is small and is masked by the stronger surface noise. Prior art instruments have been unable to filter out this surface noise to allow reading the desired signal. Using the v-p orientation, however, the surface noise is filtered out since the light hitting the fibers experiences a single light scattering event and does not change polarization. With the surface noise filtered out, an instrument including the modified readhead 110 can detect fluid levels of glucose above 400 mg/dl.

Occasionally, it is necessary to use two reagents on one reagent strip to measure low and high substrate concentrations. This is very cumbersome and more expensive since it requires the development and manufacture of two reagents and reagent strips with two pads. In accordance with the present invention, high and low substrate concentrations can be easily measured using two detectors. In another alternative embodiment of the present invention, a modified readhead 310 (FIG. 4) is provided with two detectors 18A and 18B each mounted at scattering angles "x" and "y", respectively. The readhead 310 also includes a thermal light source 12 which produces light that passes through a vertical linear polarizer 322 and impinges on a reagent pad 16 on sample 14. The vertical direction of the polarizer 322 is indicated by the symbol 326. In the readhead 310 the detector 18B is intended to detect high concentrations of the substrate, and a parallel linear polarizer 330 is mounted in the readhead 310 between the pad 16 and the detector 18B. The parallel direction of the polarizer 330 is indicated by the symbol 332. The detector 18A in the readhead 310 detects low concentrations of substrate, and a vertical linear polarizer 324 is mounted in the readhead 310 between the pad 16 and the detector 18A. The vertical direction of the polarizer 328 is indicated by the symbol 328.

If there is a surface defect on the pad 16 or debris on the surface of the pad 16, the accuracy of the reading by a readhead can be significantly affected since only a slight change in the intensity in scattered light can result in an incorrect reading. A surface defect or debris can be recognized using the modified readhead 310 with the dual detection channels. If the detector 18A gives a reading different from detector 18B, this difference indicates a surface defect in or debris on the pad 16. The sample 14 can then be disposed of and a replacement sample 14 mounted in the readhead 310.

The two detectors 18A and 18B in readhead 310 can be mounted at different scattering angles x and y, respectively, and can be different polarizations. For example, the readhead 410 (FIG. 5) is the same as readhead 310 except a vertical linear polarizer 430 with the direction indicated by symbol 432 is provided in place of the parallel polarizer 330. The readhead 410 may be used instead of the readhead 310 to detect surface defects and debris.

Although different scattering angles and polarizations may be used in the readheads 310 and 410, it has been determined that the most effective scattering angles are forty-five degrees for both x and y with a v-p orientation for the linear polarizers 322 and 330, respectively, and a v-v orientation for the linear polarizers 322 and 324.

Figure 4:
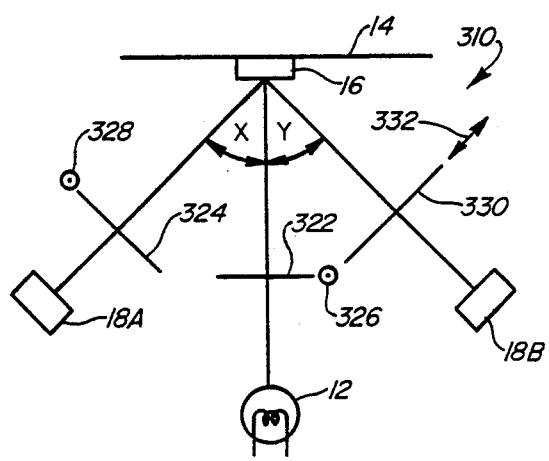
FIG. 4 is a schematic illustration of another embodiment of the reflectance photometer readhead of the present invention including first and second detectors with first and second linear polarizers having directions of polarization vertical to a scattering plane, and a third linear polarizer having a direction of polarization parallel to the scattering plane.
Figure 5:
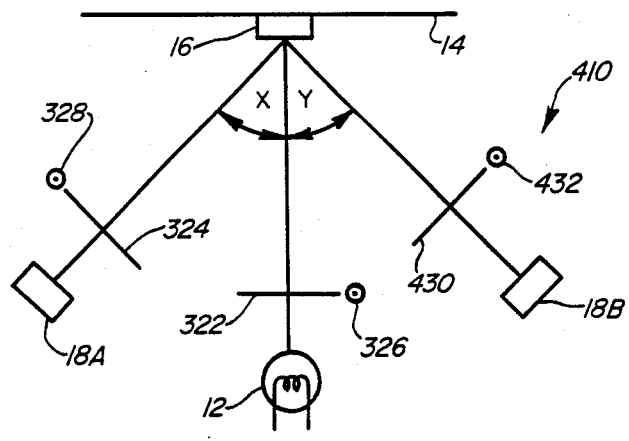
FIG. 5 is a schematic illustration similar to FIG. 4 with each of the linear polarizers having a direction of polarization vertical to the scattering plane.

The discussion of FIGS. 4 and 5 assumes a coplanar geometry; the line between the second detector 18B and the sample 16 lies within the described scattering plane. It is also possible for the second detector 18B to lie in a second scattering plane that is not coplanar with the first scattering plane. Consequently, the geometry can vary, but the objectives in designing a readhead 110 or 210 including two polarizers is to reduce surface noise as much as possible. In a readhead 310 or 410 including three polarizers, the objective is to reduce surface noise as much as possible in selecting the first 126, 226 or 326 and second 128, 228 or 328 polarizers. The third polarizer 330 or 430 is positioned to maximize surface noise recorded by the second detector 18B From the foregoing, it will be seen that the present invention attains all of the ends and objects set forth in the preceeding paragraphs. The readheads 110, 210, 310 and 410 have greater accuracy and sensitivity than the prior art readhead 10. This increased accuracy and sensitivity is possible by optical modification rather than the more difficult and expensive chemical modifications used in the prior art.

Many modifications and variations of the invention as hereinbefore set forth can be made without departing from the spirit and scope thereof and only such limitations should be imposed as are indicated by the appended claims.

What is claimed is

1. A method for determining the quantity of a selected fluid component in a sample of fluid placed on a reagent strip impregnated with a chemical reactive with said selected fluid component, comprising the steps of:
   directing polarized light onto said sample;
   determining the magnitude of at least a portion of unpolarized light reflected from said sample, said magnitude being correlative to the quantity of said selected fluid component,
   determining the magnitude of at least a portion of polarized light reflected from said sample; and
   comparing the magnitude of said unpolarized light to the magnitude of said polarized light.

2. The method as set forth in claim 1, wherein said determination of the quantity of a selected fluid component is inaccurate if the magnitude of said unpolarized light differs from the magnitude of said polarized light by more than a predetermined magnitude.

3. A method for determining the quantity of glucose in a body fluid sample placed on a reagent strip impregnated with a chemical reactive with glucose, comprising the steps of:

directing polarized light onto said sample;

determining the magnitude of at least a portion of unpolarized light reflected from said sample, said magnitude being correlative to the quantity of glucose in said body fluid sample, determining the magnitude of at least a portion of polarized light reflected from said sample; and comparing the magnitude of said unpolarized light to the magnitude of said polarized light.

4. The method as set forth in claim 3, wherein said determination of the quantity of a selected fluid component is inaccurate if the magnitude of said unpolarized light differs from the magnitude of said polarized light by more than a predetermined magnitude.

* * * * *